US007842496B2

(12) United States Patent
Miller et al.

(10) Patent No.: US 7,842,496 B2
(45) Date of Patent: Nov. 30, 2010

(54) ADVANCED SELECTIVE PLATING MEDIA

(75) Inventors: Russell G. Miller, Gambrills, MD (US); Edward T. Mallinson, Silver Spring, MD (US)

(73) Assignee: University of Maryland, College Park, MD (US)

( * ) Notice: Subject to any disclaimer, the term of this patent is extended or adjusted under 35 U.S.C. 154(b) by 93 days.

(21) Appl. No.: 11/797,354

(22) Filed: May 2, 2007

(65) Prior Publication Data

US 2007/0298452 A1     Dec. 27, 2007

Related U.S. Application Data

(63) Continuation-in-part of application No. PCT/US2006/035625, filed on Sep. 13, 2006.

(60) Provisional application No. 60/746,227, filed on May 2, 2006.

(51) Int. Cl.
*C12N 1/20*     (2006.01)
*C12N 1/00*     (2006.01)
(52) U.S. Cl. .................. 435/253.6; 435/34; 435/252.1; 435/252.4; 435/879
(58) Field of Classification Search .................. None
See application file for complete search history.

(56) References Cited

U.S. PATENT DOCUMENTS 5,208,150 A * 5/1993 Tate et al. ..................... 435/38

5,871,944 A * 2/1999 Miller et al. ................ 435/7.35

OTHER PUBLICATIONS

Bergey's Manual of Determinative Bacteriology. 9th edition, 1994, pp. 31, 177, 186, 187, 2-3, 204, 215, 215, 218.*
Atlas R.M. Handbook of Microbiological Media. 1994, pp. 431, 507, 996.*
Tan et al. "Automated detection of *Salmonella* spp. in food". Journal of Microbiological Methods. 1999, vol. 37, pp. 620-622.*
Brauss F.W. ZENTRALBL BAKT I ABT ORIG, (1943) vol. 150, No. 4, pp. 220-224 (STN Biosis Abstract accession No. 1945:11-71).*
Taylor, Welton I. et al., *The American Journal of Clinical Pathology*, 44(1):471-475 (1965).
Miller, R. G. et al., *Journal of Food Protection*, 63(10):1443-1446 (2000).
Miller, R. G. et al., *Clinical Microbiology Newsletter*, 32(5):38-39 (2010).

* cited by examiner

*Primary Examiner*—Vera Afremova
(74) *Attorney, Agent, or Firm*—Leydig, Voit & Mayer, Ltd.

(57) ABSTRACT

Selective growth media N4 agars that include a combination of high levels of yeast extract, possibly higher levels of protein, elevated levels of sugar and reduced levels of sodium chloride. The combination of ingredients provides the ability to detect *Salmonella* spp. and *Shigella* spp. with almost identical sensitivity while alleviating false-negative and false-positive problems commonly encountered with the presence of *Proteus* spp. and *Citrobacter* spp.

6 Claims, 11 Drawing Sheets
(11 of 11 Drawing Sheet(s) Filed in Color)

ADVANCED SELECTIVE PLATING MEDIA

CROSS-REFERENCE TO RELATED APPLICATIONS

This patent application is a CIP application of PCT/US2006/035625 having an international filing date of 13 Sep. 2006 and claims priority to U.S. provisional patent application Ser. No. 60/746,227 filed May 2, 2006. Both applications are incorporated by reference herein as if set forth in their entirety.

BACKGROUND OF THE INVENTION

1. Field of Invention

This invention relates to the field of growth medium for bacteria and more specifically, this invention relates to selective plating media for the detection of specific bacteria strains or species. In particular, the present invention pertains to *Salmonella* or *Shigella* preferential selective plating media and use thereof.

2. Description of Prior Art

There exist a wide variety of commercially available plating media on the market, suggested as being preferential for *Salmonella* spp. Some of the more common selective plating agars are: MAC (Mac Conkey), HE (Hektoen Enteric); SS (*Salmonella-Shigella*); and XLD (xylose-lysine-deoxycholate). However, these well known agars, while capable of supporting the growth of *Salmonella* spp. and *Shigella* spp., are not as sensitive or as specific as one may need. This is because these agars do not adequately allow the differentiation of commonly encountered background bacterial growth (e.g. *Citrobacter*, and *Proteus* spp.) from the *Salmonella* and *Shigella* species which are to be detected.

The two present Applicants have contributed to the development of two different and more selective agars for detection of *Salmonella* spp. and *Shigella* spp. The first was XLT4, which comprised TERGITOL®4 (7-ethyl-2-methyl-4-undecanol hydrogen sulfate) in a conventional xylose-Lysine agar base medium, and additional promoters of $H_2S$ production, and is disclosed in U.S. Pat. No. 5,208,150, and incorporated by reference into the specification herein, in its entirety. This media is highly preferentially for *Salmonella*. The second selective agar was named MM (Miller-Mallinson) agar, which is disclosed in U.S. Pat. No. 5,871,944 and is also incorporated by reference into the specification herein, in its entirety. MM media was designed to detect strains of *Salmonella* that produce significantly lower amounts of $H_2S$ than other strains such as *Salmonella. typhi* and *Salmonella Choleraesuis* var. *Kunzendorf.*

Applicants discovered, however, during the subsequent use of XLT4 and MM media, that while these selective growth agars could be successfully used for the great reduction of *Proteus* spp. growth, and in better differentiation of *Citrobacter* colonies in veterinary and food safety applications, they were not entirely successful for detecting *Salmonella* spp. and *Shigella* spp, in human diagnostic applications. XLT4 agar was found to be too inhibitory for *Shigella* spp. Moreover, while MM agar was found to be good at supporting growth and differentiation of *Shigella flexneri*, it did not differentiate *Shigella sonnei* colonies from colonies of *E. coli* and other lactose fermenting bacteria.

In general, the *Salmonella/Shigella* selective plating media currently available do not support the most efficient detection of salmonella species. MM and SS agar do not have the ability to differentiate *Shigella sonnei* from lactose-fermenting background colonies and reduces the sensitivity of these growth media for use in detection of an important human pathogen.

Therefore, there still exists a need for a selective growth plating media that provide sufficiently greater selectivity for *Salmonella* and *Shigella* colonies than current selective growth plating media, so that the selective growth media are capable of being used in human diagnostic applications and in food, feed and water quality control.

SUMMARY OF THE INVENTION

In accordance with the present invention, it has been discovered by Applicants, that selective growth plating media could be made comprising the ingredients contained generally in XLT4 agar, but with higher levels of a hydrolyzed protein source, yeast extract, and additional alpha lactose and sucrose, and the new addition, (D+)-cellobiose, salicin and dulcitol while the concentration of agar and sodium chloride were lowered from what was generally present in XLT4 agar. Further, the selective growth media of the present invention also allows increased concentrations of NIAPROOF®4 (7-ethyl-2-methyl-4-undecanol hydrogen sulfate, also known as 7-ethyl-2-methyl-4-undecyl sodium sulfate). These compounds are present in sufficient concentrations to allow greater sensitivity and specificity for growth and detection of *Salmonella* spp. and *Shigella* spp. over the selective plating media of the prior art.

It is therefore an object of the present invention to provide selective growth plating media that have significantly greater sensitivity and specificity in the detection of both *Salmonella* and *Shigella* colonies than currently available.

It is also an object of the present invention to provide selective growth plating media that have sufficient sensitivity and specificity in the detection of both *Salmonella* and *Shigella* such that they can be used in the detection of the presence of either *Salmonella* and *Shigella* in food, feed and water and articles for food processing, as well as articles or devices for human clinical use and in or on an article recovered from human or animal subjects for clinical diagnostic or epidemiological study. Further, the selective growth media of the present invention also allows increased concentrations of NIAPROOF®4 (7-ethyl-2-methyl-4-undecanol hydrogen sulfate, also known as 7-ethyl-2-methyl-4-undecyl sodium sulfate).

These together with other objects and advantages, which will become subsequently apparent, reside in the details of the technology as more fully hereinafter described and claimed, reference being had to the accompanying photographs forming a part hereof, wherein, if relevant like numerals refer to like parts throughout.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION AND PREFERRED EMBODIMENTS

In describing embodiments of the invention, specific terminology will be resorted to for the sake of clarity. However, the invention is not intended to be limited to the specific terms so selected, and it is to be understood that each specific term includes all technical equivalents which operate in a similar manner to accomplish a similar purpose. For example, for purposes of this application, the terms "N4 agar" or "N4 agars" refer to the presence of NIAPROOF®4 in media mixtures of the present invention and such terms can be used to help denote generally the various formulations of agar disclosed herein.

Figure 3:
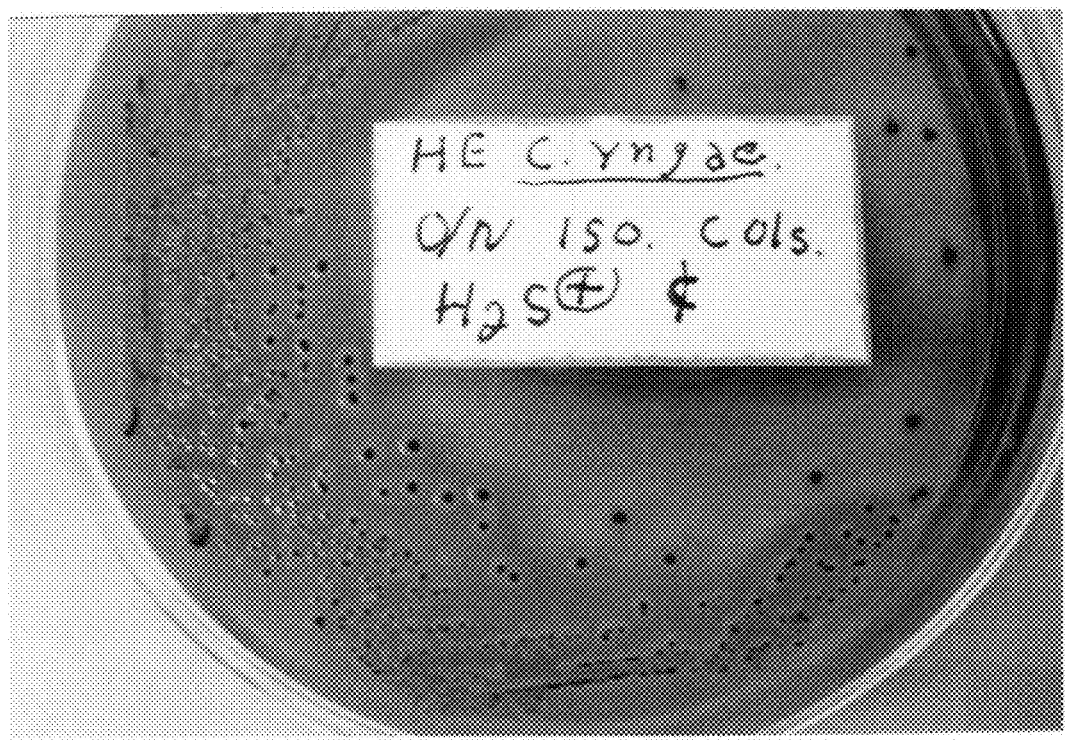
FIG. 3 is a photograph of colonies of *Citrobacter youngae* growing overnight on a plate of HE agar. Note the black centered colonies can be easily mistaken for *Salmonella* suspect colonies.

A significant and common problem with most selective plating agars (e.g., HE, SS, XLD) is the presence of black ($H_2S$-positive) colonies of *Citrobacter* spp., which are easily mistaken for *Salmonella* colonies. FIG. 3 is a photograph of an HE coated plate with colonies of *Citrobacter youngae* having black-centers that are easily mistaken for *Salmonella*-suspect colonies.

Although it was thought by Applicants that the composition of MM agar (e.g., 10.0 g/l alpha lactose and 5.0 g/l D(+)-cellobiose) partially reduced the false-positive (black) colony problem associated with *Citrobacter* spp., the problem still exists in the prior art. However, in the present invention, Applicants successfully and logically attacked this persistent problem in the art by experimenting with the concentrations and types of sugars used for the selective growth media N4 agars.

It is known to those of ordinary skill in the microbiological arts that when a bacterial colony's supply of fermentable sugars is exhausted, $H_2S$ is produced because such bacterial colonies switch to protein as an energy source on selective plating agar. For instance, it is known that when *Citrobacter* spp. are able to find a carbon source that they can utilize, they are not forced to utilize the protein component of a media to maintain metabolism. Diverting *Citrobacter* spp. from utilizing protein retards the production of $H_2S$, and consequently, formation of black colonies that could be misdiagnosed as *Salmonella* colonies.

Among the more than 50 carbon sources utilized by *Citrobacter* spp., five in particular cellobiose, as well as lactose, sucrose, salicin and dulcitol are considered by the inventors to be readily available carbon sources that, with the exception of dulcitol, are infrequently used by *Salmonella* or *Shigella*. A plurality of these five carbon sources in amounts set forth herein is considered by the inventors to be a practical, effective and complementing combination for diverting a broad range of 14 different *Citrobacter* spp. (e.g., *C. freundii, C. youngae, C. braakii* and others) away from protein as a metabolic source, thus blocking $H_2S$ (black colony) formulation.

This diversion and the blocking of black colony formation is suppressed by incorporating significantly higher concentrations of sugars in the N4 agars of the present invention. Added amounts of sugars are sucrose, cellobiose, salicin and dulcitol. As compared to the present invention, in MM there is a lower level of cellobiose and no sucrose, salicin or dulcitol. As compared to the present invention, in XLT4 there is no cellobiose, salicin or dulcitol but there is sucrose and lactose but these sugars are present in levels lower than in the present invention.

So the current composition contains higher concentrations of carbohydrates than that the prior art and the carbohydrate make up includes the novel combination of cellobiose, lactose, sucrose, salicin and dulcitol. Thus, applicants now disclose herein, a novel combination of lactose and sucrose plus cellobiose, salicin and dulcitol comprising the selective growth media of the present invention. Cellobiose is present in amounts of about 5.0 to 15, preferably in amounts of about 8.0 to 12.0 and most preferably in the amounts of about 8.0 g/L. Salicin is present in amounts of about 2.0 to 12.0, preferably in amounts of about 8.0 to 10.0 and most preferably in the amount of about 8.0 g/L. Lactose is present in amounts of about 5.0 to 15.0 preferably in amounts of about 8.0 to 12.0 and most preferably in amounts of about 8.0 g/L; and sucrose is present in amounts of about 5.0 to 15, preferably in amounts of about 5.0 to 12.0 and most preferably in an amount of about 8.0 g/L.

Xylose and dulcitol are also present to enhance early *Salmonella* growth and *Shigella* differentiation. Each may be present in amounts in amounts of about 1.0 to 8.0, preferably in amounts of about 2.0 to 4.0 and most preferably in the amount of about 2.0 g/L.

It will be understood by those of ordinary skill that any source of 7-ethyl-2-methyl-4-undecanol hydrogen sulfate solution can be used with the present invention, such as Sigma-Aldrich Ultra Type 4 NIAPROOF®4 (Product Code #N-1404, 27% wt) for use in formulating the selective N4 agars of the present invention.

In a preferred embodiment, the preferred source of 7-ethyl-2-methyl-4-undecanol hydrogen sulfate solution NIAPROOF®4 is XLT4 Agar Supplement (BD Biosciences Product Code 235310, 27% wt) for use in formulating the selective N4 agars of the present invention. NIAPROOF®4 should not be refrigerated because cool temperatures may cause it to separate. As a precaution against any separation, it is warmed to 30° C. and agitated prior to use.

Under ordinary circumstances, NIAPROOF®4 is a very potent reagent in suppressing *Proteus* spp., a common group of background *Shigella*- and *Salmonella*-masking enteric bacteria.

It is noted for clarity by the Applicants that the chemical formula for NIAPROOF®4 (formerly supplied by Union Carbide as TERGITOL®4) is identified in the Sigma® Catalog as 7-ethyl-2-methyl-4-undecyl sulfate sodium salt or as $C_{14}H_{29}NaO_4S$ (empirical formula-Hill Notation). However, the chemical formula for the NIAPROOF®4 supplied by BD, as the XLT4 Agar Supplement is identified as 7-ethyl-2-methyl-4-undecanol hydrogen sulfate, or sodium salt thereof. Applicants consider both formulas as equivalent for purposes of the present invention.

The Applicants contemplate that one may need to combine 3.0 to 20.0 g/L levels of proteose peptones and with surprisingly high (e.g., 7.5 to. 30.0 g/L) levels of yeast extract to support the growth of not only *Salmonella* colonies, but also the prompt robust, easily-detected growth of *Shigella* colonies. *Shigella* spp. will appear as non-pigmented colonies, while *Salmonella* spp., when present, appear as black or black-centered colonies. Compare the plates in FIG. 1 with the plates in FIGS. 2a and 2b. Yeast extract is ordinarily only used in low levels (usually 3.0 g/l) as a marginal growth promoter. Until the present invention, those in the art did not expect that yeast extract could successfully be used at increased concentrations to markedly increase the growth of *Shigella* spp., especially on a medium as highly selective as the N4 formula, or for most other relatively selective formulae. The combination of unusually high levels of yeast extract with proteose peptone as used in N4 agars is unknown in other enteric media. Many variations in types and levels of yeast, beef extract, peptones, and carbon sources can be substituted in the of the N4 formula of the present invention. Yeast extract is present in amounts of about 3.0 to 30.0, preferably in amounts of about 10.0 to 23.0 and most preferably in amounts of about 15 to 20 g/L. One or more hydrolyzed proteins may be present in amounts of about 1.0 to 15.0, preferably more likely in amounts of about 6.0 to 12.0 and most preferably in amounts of about 3.0 to 6.0 g/L.

Lysine is present for the detection of occasionally $H_2S$-negative *Salmonella*. It is present in amounts of about 2.0 to 10.0, preferably in amounts of about 4.0 to 6.0 and most preferably in the amount of about 5.0 g/L.

Sodium thiosulfate is present as one of the two parts of the $H_2S$ detection system of N4 agar of the present invention. It is present preferably in amounts of about 5.0 to 8.0, preferably in amounts of about 6.0 to 7.0 and most preferably in the amounts of about 6.8 g/L.

Ferric ammonium citrate is the second co-part of the $H_2S$ detection system of N4 agar of the present invention. It is present in amounts of about 0.6 to 1.0, preferably in amounts of about 0.7 to 0.9 and most preferably in the amount of about 0.8 g/L Phenol red is a non-chromogenic indicator for color differentiation between various colonies. Color differences generated by phenol red are based on pH levels rather than a chromogenic reaction. It is present in amounts of about 0.05 to 0.2, preferably in amounts of 0.08 to 0.1 and most preferably in the amount of about 0.08 g/L.

Agar is present for media solidity to allow proper streaking of the culture inoculum. It is present in amounts of about 8.0 to 20.0, preferably in amounts of about 12.0 to 18.0 and most preferably in the amounts of 14.0 g/L.

Sodium chloride, when present, is employed for proper media dampness and may be present in amounts of about zero to 5.0 and preferably in amounts of about 0 to 2.0 and most preferably in a zero amount.

The Formula of the Selective Growth

EXAMPLE 1

General Media N4 Agar

In a first embodiment of the selective plating media of the present invention, a general selective N4 agar can be made by mixing with one liter of water with the following ingredients:
  a) between about 3.0 to about 30.0 g yeast extract;
  b) between about 0.0 to 10.0 g proteose peptone No. 3;
  c) between about 0.0 to 15.0 g proteose peptone;
  d) between about 0.0 to 10 g L-lysine;
  e) between about 0.0 to about 8.0 g xylose;
  f) between about 0.0 to about 15.0 g alpha lactose;
  g) between about 0.0 to about 15.0 g sucrose;
  h) between about 0.0 to about 15.0 g (D+)-cellobiose;
  i) between about 0.0 to about 15.0 g salicin;
  j) between about 0.0 to about 8.0 g dulcitol;
  k) between about 0.0 to 5.0 g sodium chloride;
  l) between about 5.0 to 8.0 g sodium thiosulfate;
  m) between about 0.6 to 1.0 g ferric ammonium citrate;
  n) between about 0.05 to 0.2 g phenol red; and
  o) between about 10.0 to 20.0 g agar;
  p) between about 4.0 to 12.0 ml 7-ethyl-2-methyl-4-undecanol hydrogen sulfate solution (NIAPROOF® 4, Sigma-Aldrich, Product Code 4 or BD-Difco Product Code 235310).

About 1.0 L of room temperature distilled/demineralized water is added to the above compounds and then mixed to suspend them in the water. Next, between about 4.0 to 12.0 ml 7-ethyl-2-methyl-4-undecanol hydrogen sulfate solution (NIAPROOF® 4, Sigma-Aldrich, Product Code 4 or BD-Difco Product Code 235310) is added while continuing to mix the suspension. A sterile magnetic stir bar and magnetic stirrer can be used to facilitate suspending and dissolving the ingredients. Do not shake the suspension, as it will cause excessive frothing. Bring to a boil for approximately one minute to insure that all compounds have been dissolved especially the agar present in the powdered XLT4 agar base ingredient. Remove from the heat source and cool in a water bath to 45-50° C. Plates are then poured so that the finished medium is about 4-5 mm thick. The plates are allowed to remain at room temperature overnight, before storing at 2-5° C., in well-sealed plastic bags.

EXAMPLE 2

N4 Formula 273

In another preferred embodiment of the selective plating media of the present invention, a selective N4 agar is made by mixing with one liter of water with the following ingredients:
   a) between about 7.5 to about 15.0 g yeast extract;
   b) between about 3.0 to 6.0 g proteose peptone No. 3;
   c) between about 3.0 to 6.0 g proteose peptone;
   d) between about 4.0 to 6.0 g L-lysine;
   e) between about 2.0 to 4.0 g xylose;
   f) between about 10.0 to 15.0 g alpha lactose;
   g) between about 10.0 to 15.0 g sucrose;
   h) between about 10.0 to 15.0 g (D+)-cellobiose;
   i) between about 4.0 to 8.0 g salicin
   j) between about 2.0 to about 4.0 g dulcitol;
   k) between about 0.7 to 0.9 g ferric ammonium citrate;
   l) between about 6.0 to 7.0 g sodium thiosulfate
   m) between about 0.08 to 0.10 g phenol red;
   n) between about 12.0 to 14.0 g agar; and
   o) between about 4.0 to 8.0 ml 7-ethyl-2-methyl-4-undecanol hydrogen sulfate solution (NIAPROOF® 4, Sigma-Aldrich, Product Code 4 or BD-Difco Product Code 235310).

The method for making and storing the plates containing the compounds for N4 formula 273 media are otherwise identical to those described for the General Formula for N4 Agar in the previous section.

The omission of sodium chloride for N4 formula 273 enhances the extent of outgrowth of *Shigella* spp.

The selective and general N4 agar formula and N4 agar formula 273 are not chromogenic formulae. A chromogenic media is one that contains an indicator e.g. X-gal. The indicator provides a substrate for of an enzyme produced by bacterial colonies and the complex formed produces a water insoluble precipitate of an identifying color. A list of chromogenic substrates is found in U.S. Pat. No. 6,764,832 herein incorporated by reference in its entirety.

The selective N4 273 Agar has two to five times more yeast extract and two to three times as much cellobiose compared to MM media. The N4 Agar formula 273 contains sucrose, salicin, dulcitol, xylose and proteose peptone that are not present in MM agar. In addition, the N4 agar formula 273 also contains the same level of alpha lactose, but does not contain mannitol, trehalose dehydrate, beef extract or polypeptone peptone or sodium chloride as MM media.

The omission of NaCl from N4 formula 273 is a major departure from the 5.0 g/L of salt present in MM and XLT4 agars, and in MAC, HE and XLD agars.

In another embodiment, the pH indicator, neutral red or bromothymol blue are individually substituted for all the pH indicator phenol red, which is present in a preferred embodiment of the N4 agar of present invention. The use of neutral red or bromothymol blue is contemplated to possibly improve the delineation of acidic colonies of competing background colonies (*Citrobacter, Proteus, Escherichia,* etc.) from non-acidic (alkaline) colonies of *Salmonella* and *Shigella*. It is known that use of phenol red may lead to blurring of the color differences between acidic and non-acidic colonies in those instances when these colonies are in especially close proximity to each other. In an alternative embodiment, either a concentration of neutral red indicator, ranging from about 0.01 to 0.05 g/L (Sigma-Aldrich Product Code N 7005, dye content 90%) or bromothymol blue (lot 90H 3660 Sigma Chemical Co. Cat No. B8630) indicator, ranging from about 0.02 to 0.10 g/L can each be used as separate pH indicators instead of the phenol red present in N4 agar. Neutral red may be present in amounts of about 0.01 to 0.05, preferably in amounts of about 0.02 to 0.04 and most preferably in the amount of 0.03 g/L. Bromothymol blue may be present in amounts of 0.02 to 0.10, preferably about 0.04 to 0.08 and most preferably in the amount of about 0.065 g/L instead of phenol red.

Performance Differences: N4 vs XLT4, MM and Other Agars

The selective growth media N4 agars of the present invention provide greater selectivity and in the detection of both *Salmonella* spp. and *Shigella* spp. colonies than prior enteric plating media technologies.

*Salmonella* selective plating media in general, including XLT4 agar, do not support optimal detection of *Shigella* spp. This problem lessens their efficiency and reliability for the diagnosis of an important enteric human pathogen. In contrast, the selective growth media N4 agar of Applicants' present invention provides the heretofore unknown ability to allow adequate colonial growth of both *Salmonella* spp. and *Shigella* spp. The selective N4 agars of the present invention, therefore, provide advanced selectivity for both pathogens.

A significant clinical diagnostic problem involves the growth of *Shigella* spp. on chromogenic MM agar. While *Shigella* can grow well on chromogenic MM agar, at least one clinically important species, *Shigella sonnei*, produces blue-green colonies on MM that mimic colonies of lactose-fermenting bacteria, such as *E. coli*. The Applicants discovered that this problem no longer occurs when *Shigella sonnei* was grown on the non-chromogenic selective N4 agar of the present invention. Thus, Applicants' N4 agar is useful in differentiating a wider range of clinically relevant pathogens.

Other false-positive or misdiagnosis problems that may be alleviated through the use of the selective growth media of the present invention include those problems commonly encountered with the presence of *Proteus* spp. and *Citrobacter* spp. on the plates. Both strains of bacteria produce colonies resembling $H_2S$-producing *Salmonella* colonies, which can lead to clinical misdiagnosis and prolonged sample processing time. The numbers of these colonies of both bacterial strains are greatly reduced with the use of the selective growth media N4 agar of the present invention. The increase in specificity of the growth media of the present invention over several commonly used selective plating agars is thereby illustrated in the following description and in the identified figures.

Formula Differences: N4 vs. XLT4 Agar

A comparison of the prior art XLT4 plating medium with the N4 agar (Formula 273) of the present invention, shows that the N4 agar contains up to two times more proteose peptone No. 3, about two to five times more yeast extract, 100% less sodium chloride than XLT4 agar. In addition, cellobiose, salicin, dulcitol and proteose peptone, absent from XLT4 agar, are present in N4 agar and (formula 273).

If one compares the prior art XLT4 plating medium with the N4 agar (formula 273) of the present invention, one sees that this growth media allows more proteose peptone No. 3, between two to five times more yeast extract and, 33.3% to 100% more alpha lactose and sucrose than XLT4 agar. In addition, cellobiose, salicin and dulcitol, absent from XLT4 agar, are present in N4 agars. A modest increase in proteose peptone No. 3 was surprisingly found by the inventors to complement yeast extract's ability to support the growth of *Shigella* spp. Similarly, the inventors also found that unusually high levels of yeast extract were important to the ability of N4 to support acceptable colonial growth of *Shigella* spp.

Formula Differences: N4 vs. MM Agar

When comparing the prior art MM plating medium with the N4 agar (formula 273) of the present invention, one can see that the selective N4 agar of the present invention contains two to five times more yeast extract and two to three times as much cellobiose as does MM agar. In addition, salicin and dulcitol, absent from MM agar are present in N4 agar (formula 273). Formula 273 contains no sodium chloride whereas MM agar does.

Cellobiose, salicin and dulcitol are increased in amounts over that used in MM media, as an especially potent source of carbon utilized by a high percentage of *Citrobacter* spp.

The N4 agar of the present invention contains sucrose, xylose, salicin and dulcitol and peptones, not present in MM agar. N4 agar may also have about 5.0 more grams of alpha lactose than MM agar.

Another distinction between the selective growth media of the present invention and MM agar is that N4 agars of the present invention are not chromogenic media, in the sense that they require enzymatic activity to generate a color, as is MM. The N4 agars of the present invention do not contain the chromogen X-gal, or special buffers to keep the medium at a neutral pH, in the presence of bacterial growth. Furthermore, the N4 agars do not contain mannitol, trehalose-dihydrate, beef extract or polypeptone peptone, whereas the prior art MM agar does. The total protein concentration in N4 media can range from about the same or about twice that used in MM media.

Figure 8:
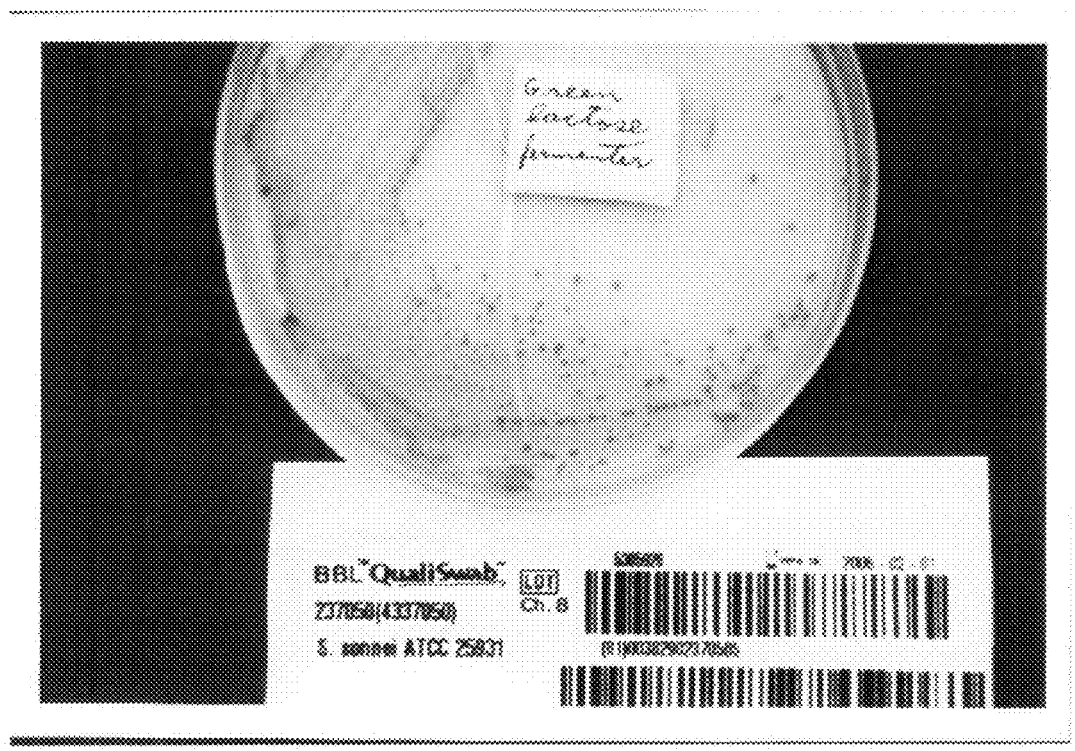
FIG. 8 is a photograph of a plate coated with MM agar and having *Shigella sonnei* colonies growing. The *Shigella* colonies exhibit a blue-green color also seen with many competing lactose-fermenting bacteria, such as *E. coli*.
Figure 9:
FIG. 9 is a photograph of 3 coated plates. The top right plate is coated with HE agar, and the top left is coated with SS agar. Each plate was inoculated with a human fecal specimen. The figure shows the false *Salmonella*-suspect ($H_2S$ positive black colonies) in the top plates, and none on the N4 agar at bottom center.
Figure 10:
FIG. 10 is a photograph of 3 coated plates. The top right plate is coated with XLD agar, and the top left is coated with SS agar, and the bottom center plate is coated with selective growth medium N4 agar of the present invention. Each plate was inoculated with a human fecal specimen. The figure shows the false *Salmonella*-suspect ($H_2S$ positive black colonies) in the top plates, and none on the N4 agar.

Colony Differentiation Strategies and Rationales for the Various Types and Levels of Ingredients Used in N4 Agar As stated previously, although MM agar supports the growth of *Shigella* spp., chromogenic (enzymatic) colony differentiation stratagem of MM agar does not permit the differentiation of clinically important *Shigella sonnei* colonies from the blue-green colored colonies of *E. coli* and other lactose-fermenting bacteria. This can be a significant clinical problem, because clinicians using MM agar would not be able to differentiate colonies of ordinarily unimportant lactose-fermenting bacteria (e.g., *E. coli*) from those of the pathogen, *Shigella sonnei*. The result would be a false negative for *Shigella* and a laboratory-related clinical misdiagnosis. An example of this is shown in the photograph of FIG. 8, where a plate coated with MM agar is shown having *Shigella sonnei* colonies growing on it.

Figure 1:
FIG. 1 is a photograph of two plates having the N4 agar of the present invention. Good-sized, black ($H_2S$ positive) *Salmonella* colonies grow on N4 agar after 24 hours at 37° C. (left plate) and 24 additional hours (right plate) at room temperature.
Figure 2A:
FIG. 2a is a photograph of an N4 coated plate having clear colonies of *Shigella sonnei* on the left and colonies of *Shigella flexneri* on the right after incubation for 24 hours at 37° C. and held for an additional 24 hours at room temperature.
Figure 2B:
FIG. 2b is a photograph of three different N4 coated plates. The plate on the top left is coated with an N4 agar formulation. The plate on the top right, and the plate at bottom center, are both coated with the selective growth medium N4 agar of the present invention. One can observe good-sized transparent colonies of *Shigella sonnei* and *Shigella flexneri* on the left and right sides (respectively) of the top two plates. Yellow (acidic), lactose-fermenting colonies of *E. coli* on N4 agar on the bottom center plate can be clearly differentiated from both species of *Shigella*.

With the N4 agar of the present invention, a non-chromogenic (direct chemical) technique, that combines the $H_2S$ production (black colony) characteristics of *Salmonella* with the negative xylose and dulcitol fermentation (colorless colony) characteristics of *Shigella sonnei* and other *Shigella* spp., is used for colonial differentiation. *Salmonella* spp. will appear as dark black colonies on N4 agar as shown in FIG. 1. *Shigella sonnei* and flexneri appear as colorless colonies over the red background of the media as shown in FIGS. 2a and 2b. Note: FIG. 2b shows the clear distinction between colorless *S. sonnei* and yellow non-pathogenic lactose-fermenting *E. coli* colonies.

Figure 4:
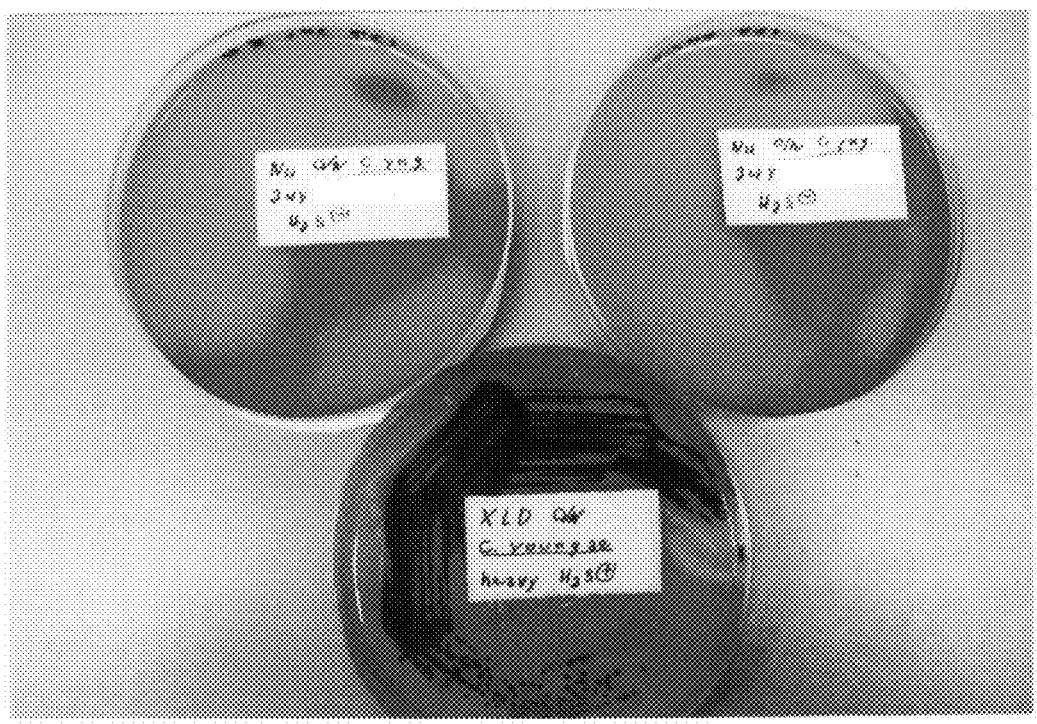
FIG. 4 is a photograph of three plates. The top plates are preliminary N4-type formulations containing (D+)-cellobiose in addition to lactose and sucrose. The top plates are compared with the formation of black (false *Salmonella*-suspect) colonies of *Citrobacter youngae* on XLD agar (lactose/sucrose only) in the bottom plate. All plates were incubated for 24 hours at 37° C.
Figure 5:
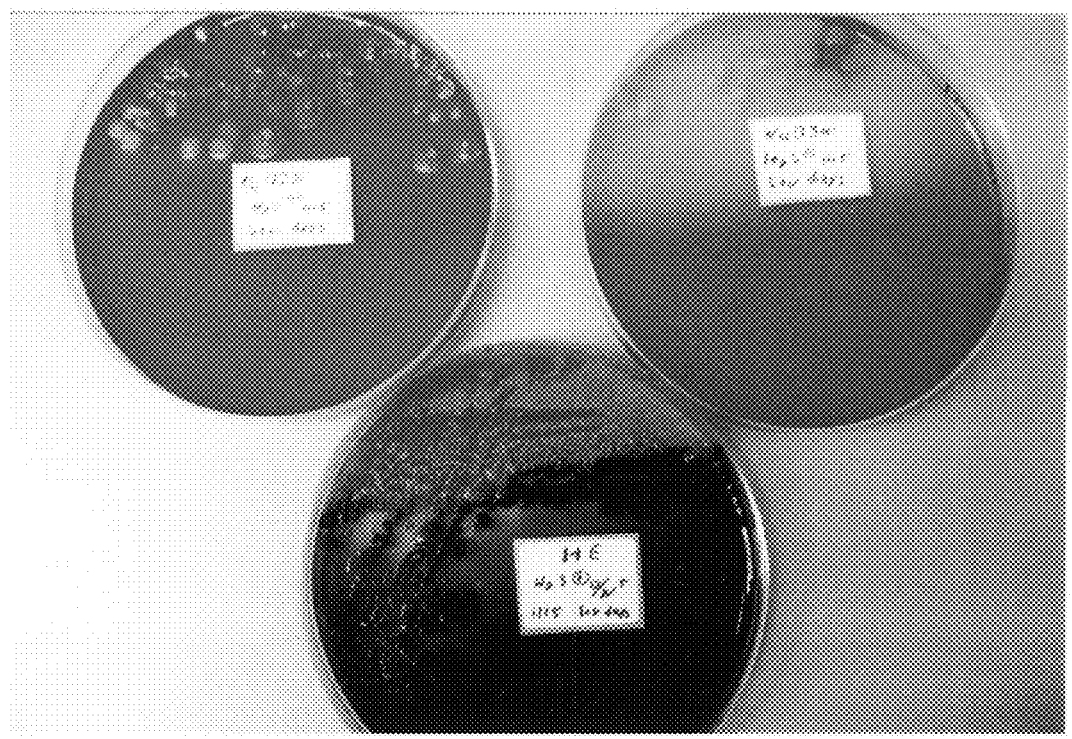
FIG. 5 is a photograph of yellow colonies of *Citrobacter youngae* on test formulations of the selective growth media N4 agar of the present invention (top plates (containing (D+)-cellobiose in addition to lactose and sucrose, compared with black colonies of the same bacteria resembling *Salmonella*, when plated on HE agar (bottom plate). All plates were incubated for 24 hours at 37° C. and then held for several days at room temperature.

Prior to the present invention, cellobiose, with the exemption of MM agar, has never been used in *Salmonella/Shigella* plating media although most such media (MAC, HE, SS, XLD, etc.) have been around many decades. It was surprisingly discovered by the inventors that, among 14 species of *Citrobacter*, *Citrobacter youngae* in particular, was more effectively diverted from utilizing the protein component(s) of a selective agar, and the production of false-suspect *Salmonella* (black) colonies, by using a plurality of additional carbohydrates such as cellobiose, salicin and dulcitol rather than only using lactose or sucrose. This was important as *Citrobacter youngae* is, on the basis of observations by the inventors and those published by others of skill in the art, a very common species of *Citrobacter*. See for example, J. Clin. Microbiol. 1999; 37(8):2619-2624 (Table 3, supporting the above explanation with respect to not only *C. youngae* (species "12"), but also to *Citrobacter braakii* (species #8), *C. werkmanii* (species #10), and *Citrobacter koseri* (species #14). The frequent occurrence of these species has been reported. See—Microbiol. Immunol. 1996; 40(12):915-21. See for instance FIGS. 4 and 5.

Until the present invention, those of ordinary skill in the microbiological art would not have contemplated that NIAPROOF®4 could be used in a growth media and still permit an acceptable growth of *Shigella* spp., as well as *Salmonella* spp. The level of NIAPROOF®4 and the choices and concentrations of carbohydrate components used in the formula for N4 agars of the present invention greatly reduces the specificity problem (false-suspect, $H_2S$ positive black colonies) encountered with most commonly used selective plating media (e.g., HE, SS, XLD). See FIGS. 4, 5, 6, 7, 9 and 10 for examples of N4's improved specificity.

As such, another novel property of the selective growth media of the present invention is that masking of *Salmonella* and *Shigella* colonies by *Proteus* overgrowth is essentially eliminated. It will be readily understood by one of ordinary skill in art, in view of the fact that the problem of false *Salmonella* positives caused by the presence of *Proteus*, and H2S-positive (false suspect) *Citrobacter* colonies, have been common vexing problems to diagnosticians for the past half-century, that Applicants' invention of the N4 plating medium which corrects these important problems, is a notable achievement. Again, see FIGS. 4, 5, 6, 7, 9 and 10 for further documentation.

An example of the effectiveness of the present invention can be seen in FIG. 2b. The plate on the top left of the photograph is coated with an N4 basic agar formulation. The plate on the top right and the plate at bottom center of the photograph are coated with a similar N4 agar formulation. Good-sized transparent colonies of *Shigella sonnei* and *Shigella flexneri* are seen on the left and right sides (respectively) of the top two plates. Yellow (acidic), lactose-fermenting colonies of *E. coli* on N4 agar on the bottom center plate can be clearly differentiated from both species of *Shigella*.

It was surprisingly discovered that it was necessary for the concentration of NIAPROOF®4 to be increased nearly two-fold in the N4 agar formula, to prevent the growth of *Proteus* spp. occurring when higher concentrations of bacterial growth factors, such as yeast extract, various peptones and carbohydrates, are used over those present in XLT4 and MM agars.

Figure 6:
FIG. 6 is a photograph of two plates. The plate on the right is coated with the selective growth media N4 agar of the present invention. The plate on the left is coated with SS agar. Both plates were inoculated with a mixed culture of *Proteus* and *Shigella* organisms and allowed to grow overnight the right plate is free of background *Proteus* growth. The black colonies of *Proteus* on SS agar are false *Salmonella*-suspects.
Figure 7:
FIG. 7 presents a photograph of two agar coated plates. On the right is a plate coated with a prototype N4 formulation assessing the concentration of NIAPROOF®4 for the suppression of competing, background bacterial growth while allowing good growth of *Shigella*. The plate on the left is coated with XLD agar. Both plates were inoculated with a mixed culture of *Proteus* and *Shigella* organisms and allowed to grow overnight. The black colonies of *Proteus* on XLD agar are false *Salmonella*-suspects.

During development of the N4 agars of the present invention, it was an objective of the Applicants to create a medium which prevented *Proteus* spp. growth because the growth of *Proteus* on most commonly-used selective plating agars, effectively masks the presence of both *Salmonella* and *Shigella* colonies. Additionally, the production of $H_2S$ by *Proteus* spp. routinely mimics $H_2S$-producing *Salmonella* colonies, thus causing a false-positive *Salmonella* diagnosis. The selective growth media of the present invention contains concentrations of NIAPROOF®4 which were found by Applicants to significantly inhibit the growth of *Proteus* spp. without the loss of the sensitivity of the N4 agar for aiding in the detection of *Salmonella* and *Shigella* spp. Refer to FIGS. 6 and 7.

The foregoing descriptions and examples should be considered as illustrative only of the principles of the invention. Since numerous applications of the present invention will readily occur to those skilled in the art, it is not desired to limit the invention to the specific examples disclosed or the exact construction and operation shown and described. Rather, all suitable modifications and equivalents may be resorted to, falling within the scope of the invention.

Having described the invention, many modifications thereto will become apparent to those skilled in the art to which it pertains without deviation from the spirit of the invention as defined by the scope of the appended claims. Thus, those skilled in the art will devise many other applications for the present invention, and it is therefore intended that the scope of this invention be not limited by the foregoing disclosure, but only by the appended claims.

The disclosures of U.S. Patents, patent applications, and all other references cited above are all hereby incorporated by reference into this specification as if fully set forth in its entirety.

What is claimed is:

1. A non-chromogenic growth medium selective for *Salmonella* or *Shigella* comprising:
   yeast extract in an amount of about 7.0 g/l to about 30.0 g/l;
   a protein source;
   one or more carbohydrate sources in amounts effective to divert *Citrobacter* spp. from utilizing said protein source, and said carbohydrates sources being present in total amounts between about 18-65 g/l; and
   7-ethyl-2-methyl-4-undecanol hydrogen sulfate.

2. The non-chromogenic growth medium of claim 1 wherein said carbohydrate sources comprise, lactose, cellobiose, xylose and sucrose.

3. The non-chromogenic growth medium of claim 2 further comprising at least one additional carbohydrate utilized by *Citrobacter* spp.

4. The non-chromogenic growth medium of claim 3 wherein the at least one additional carbohydrate utilized by *Citrobacter* spp. is at least one of salicin and dulcitol.

5. The non-chromogenic growth medium of claim 4 wherein xylose is present in amounts of between about 2.0 to 5.0 g/L.

6. The growth media of claim 2, wherein the said carbohydrate sources are present in total amounts of between about 30-61 g/l.

* * * * *